(12) United States Patent
Stopek et al.

(10) Patent No.: US 8,348,973 B2
(45) Date of Patent: Jan. 8, 2013

(54) BIOACTIVE SUBSTANCE IN A BARBED SUTURE

(75) Inventors: Joshua Stopek, Yalesville, CT (US); Matthew D. Cohen, Berlin, CT (US); Ahmad Robert Hadba, Middlefield, CT (US); Gerald Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 232 days.

(21) Appl. No.: 12/722,858

(22) Filed: Mar. 12, 2010

(65) Prior Publication Data

US 2010/0198257 A1   Aug. 5, 2010

Related U.S. Application Data

(63) Continuation-in-part of application No. 11/899,852, filed on Sep. 6, 2007.

(60) Provisional application No. 60/842,763, filed on Sep. 6, 2006.

(51) Int. Cl.
   *A61B 17/04* (2006.01)

(52) U.S. Cl. ...................................... 606/228

(58) Field of Classification Search ........... 606/228–231
   See application file for complete search history.

(56) References Cited

U.S. PATENT DOCUMENTS

| | | | |
|---|---|---|---|
| 3,123,077 A | 3/1964 | Alcamo | |
| 3,729,008 A | 4/1973 | Berkovits | |
| 3,890,977 A | 6/1975 | Wilson | |
| 3,942,532 A | 3/1976 | Hunter et al. | |
| 4,024,871 A | 5/1977 | Stephenson | |
| 4,185,637 A | 1/1980 | Mattei | |
| 4,321,002 A | 3/1982 | Froehlich | |
| 4,719,917 A | 1/1988 | Barrows et al. | |
| 4,738,666 A | 4/1988 | Fuqua | |
| 5,071,429 A | 12/1991 | Pinchuk et al. | |
| 5,089,013 A | 2/1992 | Bezwada et al. | |
| 5,123,913 A | 6/1992 | Wilk et al. | |
| 5,133,738 A | 7/1992 | Korthoff et al. | |
| 5,226,912 A | 7/1993 | Kaplan et al. | |
| 5,236,563 A | 8/1993 | Loh | |
| 5,258,000 A | 11/1993 | Gianturco | |
| 5,279,564 A | 1/1994 | Taylor | |
| 5,342,376 A | 8/1994 | Ruff | |

(Continued)

FOREIGN PATENT DOCUMENTS

EP    0 326 426 A2    8/1989

(Continued)

OTHER PUBLICATIONS

Lendlein, et al., "Shape-memory polymers as stimuli-sensitive implant materials", *Clinical Hemorheology and Microcirculation* 2005,32:105-116.

(Continued)

*Primary Examiner* — Corrine M McDermott
*Assistant Examiner* — Gregory Anderson

(57) ABSTRACT

Barbed surgical sutures are provided which include an elongated body and a plurality of barbs extending therefrom. A bioactive agent is disposed within barb angles formed between the barbs and the elongated body. The barbs may be made from a shape memory polymer having a permanent shape which may be deformed to a temporary shape, such that barbs of the suture extend at different barb angles in the different shape configurations. The barb angles of the permanent shape may be greater than the barb angles of the temporary shape, thereby exposing and/or releasing a bioactive agent after placement in tissue.

6 Claims, 5 Drawing Sheets

U.S. PATENT DOCUMENTS

| | | | |
|---|---|---|---|
| 5,415,635 | A | 5/1995 | Bagaoisan et al. |
| 5,423,858 | A | 6/1995 | Bolanos et al. |
| 5,468,248 | A | 11/1995 | Chin et al. |
| 5,569,302 | A | 10/1996 | Proto et al. |
| 5,683,417 | A | 11/1997 | Cooper |
| 5,814,056 | A | 9/1998 | Prosst et al. |
| 5,931,855 | A | 8/1999 | Buncke |
| 5,968,069 | A | 10/1999 | Dusbabek et al. |
| 6,063,105 | A | 5/2000 | Totakura |
| 6,106,505 | A | 8/2000 | Modak et al. |
| 6,143,352 | A | 11/2000 | Clark et al. |
| 6,159,139 | A | 12/2000 | Chiu |
| 6,165,202 | A | 12/2000 | Kokish et al. |
| 6,171,299 | B1 | 1/2001 | Bonutti |
| 6,203,564 | B1 | 3/2001 | Hutton et al. |
| 6,235,869 | B1 | 5/2001 | Roby et al. |
| 6,241,747 | B1 | 6/2001 | Ruff |
| 6,270,517 | B1 | 8/2001 | Brotz |
| 6,358,266 | B1 | 3/2002 | Bonutti |
| 6,388,043 | B1 | 5/2002 | Langer et al. |
| 6,506,197 | B1 | 1/2003 | Rollero et al. |
| 6,514,271 | B2 | 2/2003 | Evans et al. |
| 6,524,283 | B1 | 2/2003 | Hopper et al. |
| 6,551,282 | B1 | 4/2003 | Exline et al. |
| 6,562,051 | B1 | 5/2003 | Bolduc et al. |
| 6,589,208 | B2 | 7/2003 | Ewers et al. |
| 6,599,310 | B2 | 7/2003 | Leung et al. |
| 6,620,846 | B1 | 9/2003 | Jonn et al. |
| 6,626,916 | B1 | 9/2003 | Yeung |
| 6,773,450 | B2 | 8/2004 | Leung et al. |
| 7,341,571 | B1 | 3/2008 | Harris et al. |
| 2002/0077661 | A1 | 6/2002 | Saadat |
| 2002/0095169 | A1 | 7/2002 | Maitland et al. |
| 2002/0177876 | A1 | 11/2002 | Roby et al. |
| 2003/0074023 | A1 | 4/2003 | Kaplan et al. |
| 2003/0149447 | A1 | 8/2003 | Morency et al. |
| 2003/0236445 | A1 | 12/2003 | Couvillon |
| 2003/0236531 | A1 | 12/2003 | Couvillon |
| 2003/0236533 | A1 | 12/2003 | Wilson et al. |
| 2003/0236534 | A1 | 12/2003 | Kayan |
| 2004/0010275 | A1 | 1/2004 | Jacobs et al. |
| 2004/0030354 | A1 | 2/2004 | Leung et al. |
| 2004/0060409 | A1 | 4/2004 | Leung et al. |
| 2004/0060410 | A1 | 4/2004 | Leung et al. |
| 2004/0088003 | A1 | 5/2004 | Leung et al. |
| 2004/0138702 | A1 | 7/2004 | Peartree et al. |
| 2004/0153125 | A1 | 8/2004 | Roby |
| 2004/0162580 | A1 | 8/2004 | Hain |
| 2004/0204723 | A1 | 10/2004 | Kayan |
| 2005/0033367 | A1 | 2/2005 | Leung et al. |
| 2005/0082826 | A1 | 4/2005 | Werth |
| 2005/0149062 | A1 | 7/2005 | Carroll |
| 2005/0171562 | A1 | 8/2005 | Criscuolo et al. |
| 2005/0267531 | A1 | 12/2005 | Ruff et al. |
| 2005/0273138 | A1 | 12/2005 | To et al. |
| 2006/0111734 | A1 | 5/2006 | Kaplan et al. |
| 2006/0116718 | A1 | 6/2006 | Leiboff |
| 2007/0005110 | A1 | 1/2007 | Collier et al. |
| 2007/0038238 | A1 | 2/2007 | Freeman et al. |
| 2007/0106319 | A1 | 5/2007 | Au et al. |
| 2007/0187861 | A1 | 8/2007 | Genova |
| 2007/0203517 | A1 | 8/2007 | Williams et al. |
| 2007/0208276 | A1 | 9/2007 | Kornkven Volk |
| 2007/0224237 | A1 | 9/2007 | Hwang et al. |
| 2007/0225651 | A1 | 9/2007 | Rosenberg et al. |
| 2008/0015598 | A1 | 1/2008 | Prommersberger |
| 2009/0105655 | A1 | 4/2009 | DeSantis et al. |
| 2009/0105659 | A1 | 4/2009 | Bettuchi et al. |
| 2009/0105691 | A1 | 4/2009 | Sung |
| 2009/0259233 | A1* | 10/2009 | Bogart et al. .......... 606/144 |
| 2010/0016891 | A1 | 1/2010 | Kennedy et al. |

FOREIGN PATENT DOCUMENTS

| | | |
|---|---|---|
| EP | 0 499 048 | 8/1992 |
| EP | 0 632 999 A | 1/1995 |
| EP | 0 647 452 | 4/1995 |
| EP | 1 669 093 | 6/2006 |
| EP | 1747759 | 1/2007 |
| EP | 1747772 | 1/2007 |
| EP | 1878391 | 1/2008 |
| EP | 2050404 | 4/2009 |
| EP | 2050405 | 4/2009 |
| EP | 2050406 | 4/2009 |
| EP | 2 108 319 A1 | 10/2009 |
| EP | 2 133 028 A1 | 12/2009 |
| WO | WO 97/08238 | 3/1997 |
| WO | WO 98/00065 | 1/1998 |
| WO | WO 98/52473 | 11/1998 |
| WO | WO 99/52451 A | 10/1999 |
| WO | WO 00/57933 | 10/2000 |
| WO | WO 01/52751 A | 7/2001 |
| WO | WO 02/00286 | 1/2002 |
| WO | WO 03/001979 A2 | 1/2003 |
| WO | WO 03/088818 A2 | 10/2003 |
| WO | WO 03/088846 A1 | 10/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 | 6/2004 |
| WO | WO 2004/052594 | 6/2004 |
| WO | WO 2004/060463 | 7/2004 |
| WO | WO 2004/066927 | 8/2004 |
| WO | WO 2004/105621 | 12/2004 |
| WO | WO 2005/000001 | 1/2005 |
| WO | WO 2005/080495 | 1/2005 |
| WO | WO 2006/079469 | 8/2006 |
| WO | WO 2007/038715 | 4/2007 |
| WO | WO 2007/133103 A | 11/2007 |
| WO | WO 2008/042909 A | 4/2008 |
| WO | WO 2008/045375 A2 | 4/2008 |
| WO | WO 2008/107919 A | 9/2008 |
| WO | WO 2008/141034 A1 | 11/2008 |

OTHER PUBLICATIONS

Lendlein, et al., "Biodegradable, Elastic Shape-Memory Polymers for Potential Biomedical Applications", *Science* 2002, 296:1673-1676.

Lendlein, "Solving a knotty problem—surgical sutures from shape memorypolymers", *Materials World* 2002, 10(7):29-30.

Small, et al., "Laser-activated shape memory polymer intravascular thrombectomy device", *Optics Express* 2005,13(20):8204-8213.

Faré, et al., "In vitro interaction of human fibroblasts and platelets with a shape-memory polyurethane", *Fibroblast/Platelet Interaction With SMPu* Wiley Periodicals, Inc. (2005), pp. 1-11.

Tim Thompson, "Polyurethanes as Specialty Chemicals Principles and Applications", 2005 CRC Press, Chapter 2: Polyurethane Chemistry in Brief.

European Search Report for EP 10177651.6-1526 date of completion is Dec. 10, 2010 (3 pages).

European Search Report for EP 09007757.9-1526 date of completion is Aug. 10, 2009 (3 pages).

European Search Report for Appln. No. 09250460 dated Jun. 2, 2009.

European Search Report from application No. 07 25 4341 dated Apr. 20, 2009.

European Search Report from application No. 07 25 4703 dated Feb. 10, 2009.

European Search Report (EP 07 25 3438 dated Feb. 1, 2008).

JLTI204-211-229(175): R. R. Szarmach et al., Journal of Long-Term Effects of Medical Implants, "An Innovative Surgical Suture and Needle Evaluation and Selection Program" 12(4), pp. 211-229 (2002).

George Odian, "Principles of Polymerization", III Edition, pp. 569-573 (1991).

International Search Report from Appln. No. EP 06 012688 dated Aug. 1, 2007.

Partial European Search Report dated Jan. 22, 2008.

European Search Report for Appln. No. 09251035.3 dated Jun. 3, 2009.

European Search Report for Application No. EP 08 25 3618 dated Jul. 25, 2011.

European Search Report for European Application No. 10250002.2 dated Mar. 24, 2010. (9 pages).

* cited by examiner

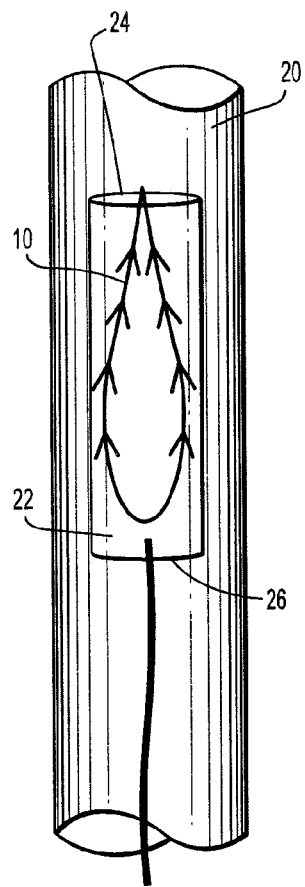
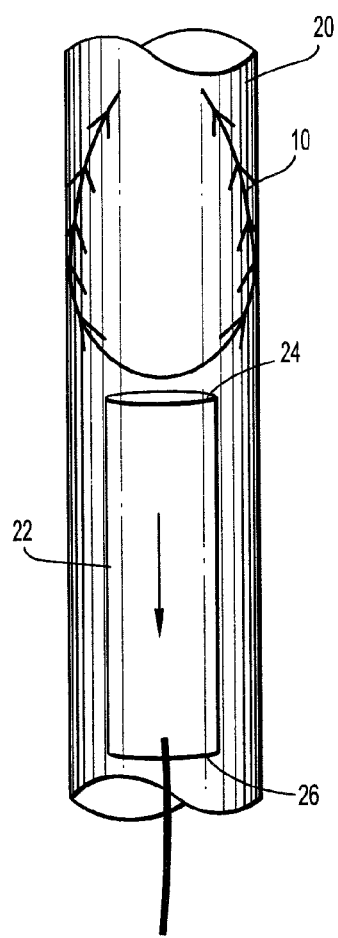
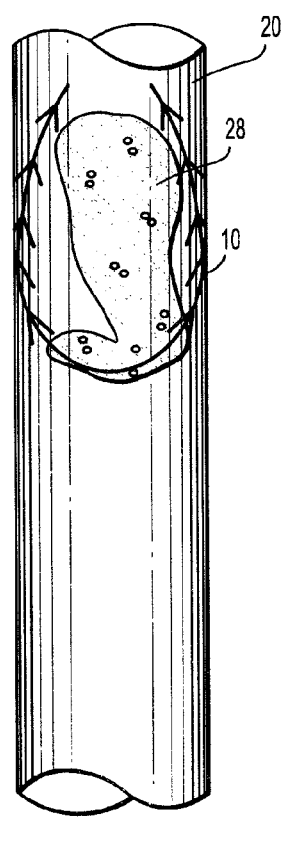
FIG. 3A  FIG. 3B  FIG. 3C

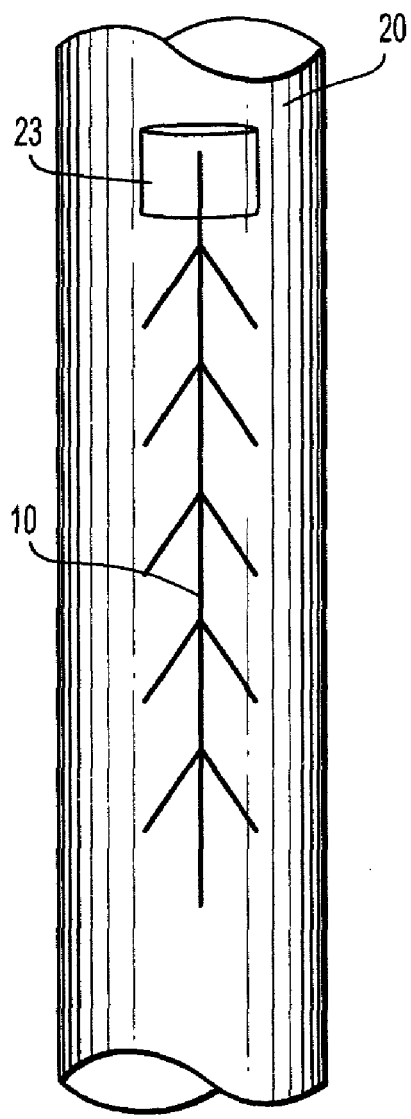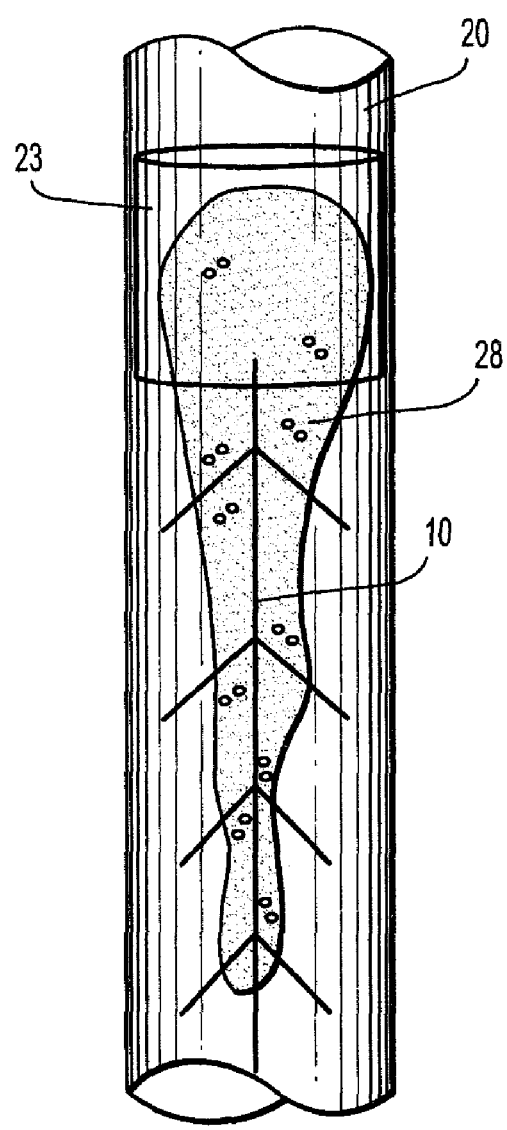
FIG. 4A  FIG. 4B

BIOACTIVE SUBSTANCE IN A BARBED SUTURE

CROSS-REFERENCE TO RELATED APPLICATIONS

This application is a continuation in part of U.S. patent application Ser. No. 11/899,852 filed Sep. 6, 2007, which claims priority to, and benefit of, U.S. Provisional Application No. 60/842,763 filed Sep. 6, 2006, the entire disclosures of each of which are incorporated by reference herein.

TECHNICAL FIELD

The present disclosure relates to barbed sutures having a bioactive agent such as an antimicrobial agent thereon, and to methods for preparing and using such sutures. In embodiments, the sutures and/or the barbs thereon may be formed, at least in part, of a shape memory polymeric material.

BACKGROUND OF RELATED ART

Barbed sutures, which are generally made of the same materials as conventional sutures, offer several advantages for closing wounds compared with conventional sutures. A barbed suture includes an elongated body that has one or more spaced barbs, which project from the surface of the suture body along the body length. The barbs are arranged to allow passage of the barbed suture in one direction through tissue but resist movement of the barbed suture in the opposite direction. Thus, one advantage of barbed sutures has been the provision of a non-slip attribute.

Barbed sutures are known for use in cosmetic, laparoscopic and endoscopic procedures. Using barbed sutures enables the placement of tension in tissue with less slippage of the suture in the wound. The number of suture barbs may be influenced by the size of the wound and the strength required to hold the wound closed. Like a conventional suture, a barbed suture may be inserted into tissue using a surgical needle.

Bioactive agents such as antimicrobial agents have been associated with surgical devices such as to prevent microbial infections during the wound healing process. It is also known to coat surgical sutures with antimicrobial compounds to prevent and treat microbial infections.

While antimicrobial agents have been used for surgical sutures and wound dressings to prevent infections, a continuing need exists for improved barbed sutures that can remain in vivo for extended periods of time with enhanced antimicrobial efficacy. There is also a need for easy and inexpensive methods of improving the antimicrobial characteristics of barbed sutures for extended periods of time thus permitting the use of lower amounts of antimicrobial agents to achieve the desired antimicrobial effect in vivo. There is also a need for delivery of other bioactive agents to wound sites to promote healing and the like.

SUMMARY

Barbed surgical sutures are provided which include an elongated body and a plurality of barbs extending therefrom. A bioactive agent is disposed within barb angles formed between the barbs and the elongated body. In embodiments, the barbs are made from a shape memory polymer having a permanent shape which may be deformed to a temporary shape, such that barbs of the suture extend at different barb angles in the different shape configurations. The barb angles of the permanent shape may be greater than the barb angles of the temporary shape, thereby exposing and/or releasing a bioactive agent after placement in tissue. The barbs may extend outwardly and away from a surface of the elongated body of the suture in the permanent shape, and the barbs may extend substantially parallel with the longitudinal axis of the elongated body of the suture in the temporary shape.

The shape memory polymer may be a bioabsorbable material, a non-degradable material, and combinations thereof. In embodiments, the shape memory polymer is a block copolymer of polydioxanone and polylactides. In other embodiments, the shape memory polymer is a block copolymer of trimethylene carbonate and polylactide.

The bioactive agent may include biocidal agents, antimicrobial agents, antibiotics, anti-proliferatives, medicaments, growth factors, anti-clotting agents, clotting agents, analgesics, anesthetics, anti-inflammatory agents, wound repair agents, chemotherapeutics, biologics, protein therapeutics, monoclonal and polyclonal antibodies, DNA, RNA, peptides, polysaccharides, lectins, lipids, probiotics, diagnostic agents, angiogenics, anti-angiogenic drugs, polymeric drugs, and combinations thereof.

Methods of releasing a bioactive agent from a suture are also provided. In accordance with the present methods, a suture including an elongated body, a plurality of barbs extends from the elongated body and forming a barb angle between the barbs and the elongated body, and an effective amount of a bioactive agent disposed within the barb angles is provided. At least a portion of the plurality of barbs is made from a shape memory polymer such that the barbs extend at different barb angles when in a temporary shape than in a permanent shape. The suture is placed into tissue such that the barbs extend from the temporary shape into the permanent shape, thereby releasing the bioactive agent into the tissue.

In embodiments, the suture is provided in a temporary shape in which the plurality of barbs are substantially parallel with a longitudinal axis of the suture. The suture may then transform into a permanent shape in which the plurality of barbs in the permanent shape extend outwardly and away from a surface of the suture.

In embodiments, the bioactive is released into the tissue from the barb angles upon transitioning of the plurality of barbs from the temporary shape to the permanent shape.

BRIEF DESCRIPTION OF THE DRAWINGS

Various embodiments of the present disclosure will be described herein below with reference to the figures wherein:

FIGS. 3A-3C are plan views of a tubular insertion device utilized with a barbed suture in accordance with the present disclosure;

FIGS. 4A-4B are plan views of a sheath utilized with a barbed suture; and

DETAILED DESCRIPTION

Figure 1:
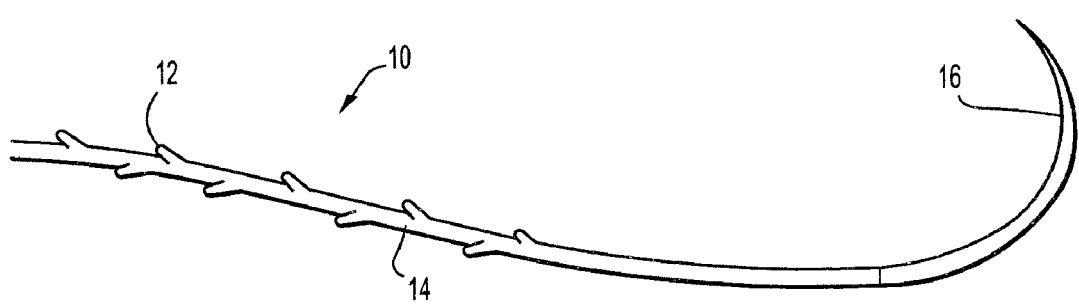
FIG. 1 is a perspective view of a barbed suture in accordance with the present disclosure attached to a needle.

Described herein are barbed surgical sutures. Sutures in accordance with the present disclosure may be of monofilament or multifilament construction. The suture may have an elongated suture body having both a proximal and distal end, with barbs projecting from the elongated body towards at least one end thereby forming an included angle of less than about 90 degrees between the barbs and the suture body. In embodiments, a bioactive agent may be deposited within the barb angles, that is, the angle formed between the barb and suture body. Placement of a bioactive agent in the angle formed between the barbs and suture body places the bioactive agent at precisely defined locations within a tissue wound closure, which thereby provides a unique controlled and sustained release dosage form.

Barbed sutures in accordance with the present disclosure may be formed of degradable materials, non-degradable materials, and combinations thereof. Suitable degradable materials which may be utilized to form the medical device include natural collagenous materials, cat gut or synthetic resins including those derived from alkylene carbonates such as trimethylene carbonate, tetramethylene carbonate, and the like, caprolactone, valerolactone, dioxanone, polyanhydrides, polyamides, polyesters, polyacrylates, polymethylmethacrylates, polyurethanes, glycolic acid, lactic acid, glycolide, lactide, polyhydroxy butyrates (PHB), polyorthoester, polyhydroxy alkanoates, homopolymers thereof, copolymers thereof, and combinations thereof. In some embodiments, glycolide and lactide based polyesters, especially copolymers of glycolide and lactide may be utilized to form a suture of the present disclosure.

In embodiments, suitable materials which may be utilized to form the sutures in accordance with the present disclosure include homopolymers, copolymers, and/or blends possessing glycolic acid, lactic acid, glycolide, lactide, dioxanone, trimethylene caprolactone, and various combinations of the foregoing. For example, in some embodiments, a copolymer of glycolide and trimethylene carbonate may be utilized. Methods for forming such copolymers are within the purview of those skilled in the art and include, for example, the methods disclosed in U.S. Pat. Nos. 4,300,565 and 5,324,307, the entire disclosures of each or which are incorporated by reference herein. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments, from about 30% to about 35% by weight of the copolymer.

Other suitable materials include copolymers of lactide and glycolide, with lactide present in an amount from about 6% to about 12% by weight of the copolymer and glycolide being present in amounts from about 88% to about 94% by weight of the copolymer. In some embodiments, lactide is present from about 7% to about 11% by weight of the copolymer with glycolide being present in amounts from about 89% to about 98% by weight of the copolymer. In some other embodiments, lactide is present in an amount of about 9% by weight of the copolymer with the glycolide being present in an amount of about 91% by weight of the copolymer.

In embodiments, suitable materials for forming sutures according to the present disclosure include, in embodiments, copolymers of glycolide, dioxanone, and trimethylene carbonate. Such materials may include, for example, copolymers possessing glycolide in amounts from about 55% to about 65% by weight of the copolymer, in embodiments, from about 58% to about 62% by weight of the copolymer, in some embodiments, about 60% by weight of the copolymer; dioxanone in amounts from about 10% to about 18% by weight of the copolymer, in embodiments, from about 12% to about 16% by weight of the copolymer, in some embodiments about 14% by weight of the copolymer; and trimethylene carbonate in amounts from about 17% to about 35% by weight of the copolymer, in embodiments, from about 22% to about 30% by weight of the copolymer, in some embodiments, about 26% by weight of the copolymer.

Other suitable materials include a copolymer of glycolide, lactide, trimethylene carbonate, and $\epsilon$-caprolactone may be utilized to form sutures in accordance with the present disclosure. Such materials may include, for example, a random copolymer possessing $\epsilon$-caprolactone in amounts from about 14% to about 20% by weight of the copolymer, in embodiments, from about 16% to about 18% by weight of the copolymer, in some embodiments, about 17% by weight of the copolymer; lactide in amounts from about 4% to about 10% by weight of the copolymer, in embodiments, from about 6% to about 8% by weight of the copolymer, in some embodiments about 7% by weight of the copolymer; trimethylene carbonate in amounts from about 4% to about 10% by weight of the copolymer, in embodiments from about 6% to about 8% by weight of the copolymer, in some embodiments about 7% by weight of the copolymer; and glycolide in amounts from about 60% to about 78% by weight of the copolymer, in embodiments, from about 66% to about 72% by weight of the copolymer, in some embodiments about 69% by weight of the copolymer.

Suitable non-degradable materials which may be utilized to form the sutures of the present disclosure include polyolefins, such as polyethylene, polypropylene, copolymers of polyethylene and polypropylene, and blends of polyethylene and polypropylene, ultra high molecular weight polyethylene, polyamides (also known as nylon), polyesters such as polyethylene terephthalate, polytetrafluoroethylene, polyether-esters such as polybutester, polytetramethylene ether glycol, 1,4-butanediol, polyvinylidene difluoride (PVDF), polyurethanes, and combinations thereof. In other embodiments, non-degradable materials may include silk, cotton, linen, carbon fibers, and the like. In some useful embodiments, polypropylene can be utilized to form the suture. The polypropylene can be isotactic polypropylene or a mixture of isotactic and syndiotactic or atactic polypropylene.

In embodiments, the barbed sutures, in whole or in part (e.g., the suture body, barbs, and/or portions thereof), may be constructed using shape memory polymers which are capable of adopting a shape in vivo suitable for adhering tissue or assisting in securing the barbed suture of the present disclosure to tissue. Shape memory polymeric materials utilized to form a barbed suture of the present disclosure possess a permanent shape and a temporary shape. In embodiments, the temporary shape is of a configuration which enhances the ability of the surgeon to introduce the suture into a patient's body. The permanent shape, which is assumed in vivo upon application of energy, such as heat or light, is of a configuration which enhances the retention of the suture in tissue and/or adhesion of a surgical device to tissue.

Shape memory polymers are a class of polymers that, when formed into an object such as a suture, can be temporarily deformed by mechanical force and then caused to revert back to an original shape when stimulated by energy. Shape memory polymers exhibit shape memory properties by virtue of at least two phase separated microdomains in their microstructure. The first domain is composed of hard, covalently cross-linked or otherwise chain motion-limiting structures, which act as anchors to retain the object's original shape. The second domain is a switchable soft structure, which can be deformed and then fixed to obtain a secondary or temporary shape.

In the case of heat stimulated shape memory polymers, a transition temperature ($T_{Trans}$) exists at which the shape change occurs during heating. The shape memory polymers can thus be tailored by altering material properties at the molecular level and by varying processing parameters. An object's primary shape may be formed with heat and pressure at a temperature at which the soft domains are flexible and the hard domains are not fully formed. The object may then be cooled so that the hard domains are more fully formed and the soft domains become rigid. The secondary or temporary shape can be formed by mechanically deforming the object, which is most readily accomplished at a temperature approaching or above $T_{Trans}$. Mechanical stresses introduced into the object are then locked into place by cooling the object to temperatures below $T_{Trans}$, so that the soft segments solidify to a rigid state. Once the object is heated to $T>T_{Trans}$, the soft segments soften and relax back to their original configuration and the object returns to its primary or original shape, sometimes referred to herein, as its permanent shape. The temperature at which a shape memory material reverts to its permanent shape may be referred to, in embodiments, as its permanent temperature ($T_{perm}$).

Polymers possessing shape memory properties which may be used to construct barbed sutures disclosed herein include, for example, synthetic materials, natural materials (e.g., biological) and combinations thereof, which may be biodegradable and/or non-biodegradable. As used herein, the term "biodegradable" includes both bioabsorbable and bioresorbable materials. By biodegradable, it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Suitable non-degradable materials which may possess shape memory properties include, but are not limited to, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polytetramethylene ether glycol; polybutesters, including copolymers of butylene terephthalate and polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other.

Suitable bioabsorbable polymers which may possess shape memory properties include, but are not limited to, aliphatic polyesters; polyamides; polyamines; polyalkylene oxalates; poly(anhydrides); polyamidoesters; copoly(ether-esters); poly(carbonates) including tyrosine derived carbonates; poly (hydroxyalkanoates) such as poly(hydroxybutyric acid), poly (hydroxyvaleric acid), and poly(hydroxybutyrate); polyimide carbonates; poly(imino carbonates) such as poly (bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

Suitable aliphatic polyesters may include, but are not limited to, homopolymers and copolymers of lactide (including lactic acid, D-, L- and meso lactide); glycolide (including glycolic acid); epsilon-caprolactone; p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicyclooctane-7-one; and polymer blends and copolymers thereof.

Other suitable biodegradable polymers include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In embodiments, combinations of both degradable and non-degradable materials, including those having shape memory characteristics, may be utilized.

In embodiments, the shape memory polymer may be a copolymer of two components with different thermal characteristics, such as oligo (epsilon-caprolactone) dimethacrylates and butyl acrylates, including poly(epsilon-caprolactone) dimethacrylate-poly (n-butyl acrylate), or a diol ester and an ether-ester diol such as oligo (epsilon caprolactone) diol/oligo (p-dioxanone) diol copolymers. These multi-block oligo (epsilon-caprolactone) diol/oligo (p-dioxanone) diol copolymers possess two block segments: a "hard" segment and a "switching" segment linked together in linear chains. Such materials are disclosed, for example, in Lendlein, "Shape Memory Polymers—Biodegradable Sutures," Materials World, Vol. 10, no. 7, pp. 29-30 (July 2002), the entire disclosure of which is incorporated by reference herein.

In other embodiments, blends of bioabsorbable materials may be utilized including, but not limited to, urethanes blended with lactic acid and/or glycolic acid, homopolymers thereof or copolymers thereof, and acrylates blended with caprolactones such as polycaprolactone dimethacrylate poly (butyl acrylate) blends, and combinations thereof.

Other examples of suitable shape memory polymers and means for forming permanent and temporary shapes therewith are set forth in Lendlein et al., "Shape memory polymers as stimuli-sensitive implant materials," Clinical Hemorheology and Microcirculation, 32 (2005)105-116, Lendlein et al., "Biodegradable, Elastic Shape memory Polymers for Potential Biomedical Applications," Science, Vol. 269 (2002) 1673-1676, and Lendlein et al., "Shape-Memory Polymers," Angew. Chem. Int. Ed., 41 (2002)2035-2057, the entire disclosures of each of which are incorporated by reference herein.

Table 1 below further illustrates compositions which demonstrate shape memory effects. The block copolymers of each composition are in annealed wire format, the proposed soft and hard segments, and the glass transition temperature ($T_g$), having been measured by differential scanning calorimetry which is equal to $T_{Trans}$.

TABLE 1

| Composition (mol %) | Soft Domain | Hard Domain | $T_g$ ($T_{Trans}$) [° C.] |
|---|---|---|---|
| 15% Polydioxanone 85% Poly (L-lactide) | Polydioxanone and Amorphous Polylactide | Crystalline Polylactide | 54 |
| 20% Polydioxanone 80% Poly (L-lactide) | Polydioxanone and Amorphous Polylactide | Crystalline Polylactide | 45 |
| 15% Trimethylene Carbonate 85% Poly (L-lactide) | Trimethylene Carbonate and Amorphous Polylactide | Crystalline Polylactide | 54 |
| 20% Trimethylene Carbonate 80% Poly (L-lactide) | Trimethylene Carbonate and Amorphous Polylactide | Crystalline Polylactide | 55 |

The copolymers in Table 1 may undergo a partial shift when approaching $T_g$ and $T_{Trans}$ may be depressed when the materials are in aqueous solution. Since these polymers degrade by water absorption and bulk hydrolysis, water molecules entering the polymer matrices may act as plasticizers, causing the soft segments to soften at lower temperatures than in dry air. Thus, polymers exhibiting $T_{Trans}$ depression in aqueous solution may maintain a temporary shape through temperature excursions in the dry state, such as during shipping and storage, and shape shift to its permanent shape at body temperatures upon implantation.

Thus, in embodiments, the shape memory polymer may include a block copolymer of polydioxanone and polylactide with the polydioxanone present in an amount from about 5 mol % to about 20 mol % of the copolymer, in embodiments from about 15 mol % to about 19 mol % of the copolymer, and the polylactide present in an amount from about 80 mol % to about 95 mol % of the copolymer, in embodiments from about 81 mol % to about 85 mol % of the copolymer. In other embodiments, the shape memory polymer may include a block copolymer of trimethylene carbonate and polylactide, with the trimethylene carbonate present in an amount from about 5 mol % to about 20 mol % of the copolymer, in embodiments from about 15 mol % to about 19 mol % of the copolymer, and the polylactide may be present in an amount from about 80 mol % to about 95 mol % of the copolymer, in embodiments from about 81 mol % to about 85 mol % of the copolymer.

It is envisioned that $T_{Trans}$ may be tailored by changing block segment molar ratios, polymer molecular weight, and time allowed for hard segment formation. In embodiments, $T_{Trans}$ may be tailored by blending various amounts of low molecular weight oligomers of the soft segment domain into the copolymer. Such oligomers may act as plasticizers to cause a downward shift in $T_{Trans}$.

Additionally, the copolymers forming the sutures of the present disclosure may include emulsifying agents, solubilizing agents, wetting agents, taste modifying agents, plasticizers, active agents, water soluble inert fillers, preservatives, buffering agents, coloring agents, and stabilizers. Addition of a plasticizer to the formulation can improve flexibility. The plasticizer or mixture of plasticizers may be polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums.

In some embodiments, crystalline degradable salts or minerals may be added to the block copolymer compositions to create polymer composites which may improve shape memory properties. An example of such a composite using polylactide homopolymer and crystalline hydroxyapatite is described in Zheng et al., "Shape memory properties of poly (D,L-lactide/hydroxyapatite composites," Biomaterials, 27 (2006)4288-4295, the entire disclosure of which is incorporated by reference herein.

Other shape memory materials, including shape memory metals and metal alloys such as Nitinol, may also be used to form the sutures of the present disclosure.

In embodiments, a molding process may be utilized to produce the sutures of the present disclosure. Plastic molding methods are within the purview of those skilled in the art and include, but are not limited to, melt molding, solution molding, and the like.

Injection molding, extrusion molding, compression molding and other methods can also be used as the melt molding technique. Once placed in the mold with the proper dimensions and configuration, the polymeric material used to form the suture may be heated to a suitable temperature, referred to as the permanent temperature ($T_{perm}$) which may, in embodiments, be the melting temperature of the shape memory polymeric material utilized to form the suture. Heating of the suture may be at suitable temperatures including, for example, from about 40° C. to about 180° C., in embodiments from about 80° C. to about 150° C., for a period of time of from about 2 minutes to about 60 minutes, in embodiments from about 15 minutes to about 20 minutes, to obtain the permanent shape and dimensions.

The temperature for deformation treatment of the suture molded with a previously memorized shape is one that makes possible ready deformation without producing cracks and should not exceed the temperature adopted for the shape memorization (e.g., $T_{perm}$). Deformation treatment at a temperature exceeding that for the $T_{perm}$ may cause the object to memorize/program a new deformed shape.

After the suture with the desired shape has been formed, the suture may be deformed above $T_{trans}$ to obtain an alternate, temporary shape. Suitable temperatures for deformation will vary depending on the shape memory polymer utilized, but generally may be above the transition temperature of the polymer ($T_{trans}$), but below the $T_{perm}$. In embodiments, the shape memory polymer may be cooled from its $T_{perm}$ to a lower temperature which remains above the $T_{trans}$ and deformed, in embodiments by hand and/or mechanical means. In other embodiments, the suture may be deformed at room temperature (about 20° C. to about 25° C.) to obtain its temporary shape, although the temperature may differ depending upon the particular polymer employed. The suture may then be cooled to a temperature below the $T_{trans}$ of the material utilized to form the sutures, at which time the suture of the present disclosure is ready for use. As the $T_{trans}$ is usually greater than room temperature, in embodiments cooling to room temperature may be sufficient to lock in the temporary shape.

There are no particular limitations on the manner in which the deformation can be achieved. Deformation can be achieved either by hand or by means of a suitable device selected to provide the desired temporary configuration to the suture.

In order to keep the shape of the suture in its temporary shape, the shape memory sutures of the present disclosure should be stored at a temperature which will not cause a transition to the permanent shape. In embodiments, the shape memory suture may be stored in a refrigerator.

In embodiments, the shape memory polymeric materials of the present disclosure may be compressed or expanded into temporary forms that are smaller or larger in diameter than their permanent shape.

The sutures thus prepared recover their permanent shape upon application of energy, such as on heating, either by placement in a patient's body, or the addition of exogenous heat at a prescribed temperature, in embodiments above the $T_{trans}$ of the shape memory polymer utilized. As the sutures of the present disclosure are utilized in a living body, heating with body heat (about 37° C.) is possible. In such a case, the temperature for permanent shape programming should be as low as possible and the recovery of the permanent shape may occur fairly slowly. In embodiments, recovery of the permanent shape may occur from about 1 second to about 5 seconds after insertion into tissue.

In embodiments, the shape memory polymer suture is barbed and then annealed near its crystallization temperature to program a permanent shape to the suture and/or its barbs. For example, the permanent shape of the suture may include the barbs extending away from the suture body. A temporary shape may then be imparted to the suture. For example, the barbed suture may be fed through a tube having an inner diameter sufficiently small to compress the barbs against the suture body. The tube may then be heated above the transition temperature of the shape memory polymeric material to soften the barbs, and then the tube and suture may be cooled to set the temporary shape. The suture may then be removed from the tube with the barbs approximated, or in alignment, with the suture body. After deployment in the body, the barbs will extend back to their primary extended shape thereby limiting movement of the suture within tissue.

However, in some embodiments a higher shape memory temperature may be desirable in order to make the shape recover at a slightly higher temperature than body temperature. Thus, in some cases, releasing the suture from deformation to recover the primary (originally memorized) shape can be achieved by heating. On heating at a temperature of from about 30° C. to about 50° C., in embodiments from about 39° C. to about 43° C., the temporary shape may be released and the primary t shape recovered. The higher the temperature above $T_{Trans}$ for heating, the shorter the time required for recovery of the primary/permanent shape. The means for this heating is not limited. Heating can be accomplished by using a gas or liquid heating medium, heating devices, ultrasonic waves, electrical induction, and the like. Of course, in an application involving a living body, care must be taken to utilize a heating temperature which will not cause burns. Examples of liquid heating media include, physiological saline solution, alcohol, combinations thereof, and the like.

Similarly, in other embodiments, electrically active polymers, also known as electroactive polymers, which can alter their configuration upon application of electricity, may be utilized to fashion sutures in accordance with the present disclosure. Suitable examples of electroactive polymers include poly(aniline), substituted poly(aniline)s, polycarbazoles, substituted polycarbazoles, polyindoles, poly(pyrrole)s, substituted poly(pyrrole)s, poly(thiophene)s, substituted poly(thiophene)s, poly(acetylene)s, poly(ethylene dioxythiophene)s, poly(ethylenedioxypyrrole)s, poly(p-phenylene vinylene)s, and the like, or combinations including at least one of the foregoing electroactive polymers. Blends or copolymers or composites of the foregoing electroactive polymers may also be used.

Similar to the change in shape which a shape memory material may undergo upon the application of energy, such as heat, in embodiments an electroactive polymer may undergo a change in shape upon the application of electricity from a low voltage electrical source (such as a battery). Suitable amounts of electricity which may be applied to effect such change will vary with the electroactive polymer utilized, but can be from about 5 volts to about 30 volts, in embodiments from about 10 volts to about 20 volts. The application of electricity will result in the suture constructed of the electroactive polymer changing its shape from a temporary shape to its permanent shape.

While an electroactive polymer does not have the same permanent shape and temporary shape as those terms are described above with respect to shape memory polymers, as used herein the term "permanent shape" as applied to an electroactive polymer means, in embodiments, the shape the electroactive polymer adopts upon the application of electricity, and the term "temporary shape" as applied to an electroactive polymer means, in embodiments, the shape of the electroactive polymer adopts in the absence of electricity.

In some embodiments, the sutures may include metals (e.g. steel and degradable magnesium), metal alloys, or the like.

Filaments used for forming sutures of the present disclosure may be formed using any technique within the purview of those skilled in the art, such as, for example, extrusion, molding and/or solvent casting.

In embodiments, the suture of the present disclosure may include a yarn made of more than one filament, which may contain multiple filaments of the same or different materials.

As used herein, the terms "fibers", "filaments" and "yarns" each may be used to construct sutures, in whole or in part. The term "fibers," in this context, are generally used to designate natural or synthetic structures that have a length approximately 3 orders of magnitude greater than their diameter or width. The term "filaments" are typically used to describe "fibers" of indefinite or extreme length, and "yarns" as a generic term for a continuous strand of twisted or untwisted "fibers" or "filaments" in a form suitable for knitting, weaving, braiding or otherwise intertwining.

In embodiments, sutures of the present disclosure may possess a core/sheath configuration, fibers may possess a core/sheath configuration, yarns may possess a core/sheath configuration, or both. Any material described herein, including the shape memory materials described above, may be utilized to form the core, the sheath, or both.

Sutures of the present disclosure may be monofilament or multifilament (e.g. braided). Methods for making sutures from these suitable materials are within the purview of those skilled in the art (e.g. extrusion and molding). The filaments may be combined to create a multifilament suture using any technique within the purview of one skilled in the art such as commingling, twisting, braiding, weaving, entangling, and knitting. For example, filaments may be combined to form a yarn or they may be braided. In another example, filaments may be combined to form a yarn and then those multifilament yarns may be braided. Those skilled in the art reading this disclosure will envision other ways in which filaments may be combined. Fibers may also be combined to produce a non-woven multifilament large diameter suture. In certain embodiments, a multifilament structure useful in forming a suture according to the present disclosure may be produced by braiding. The braiding can be done by any method within the purview of those skilled in the art. For example, braid constructions for sutures and other medical devices are described in U.S. Pat. Nos. 5,019,093; 5,059,213; 5,133,738; 5,181,923; 5,226,912; 5,261,886; 5,306,289; 5,318,575; 5,370,031; 5,383,387; 5,662,682; 5,667,528; and 6,203,564; the entire disclosures of each of which are incorporated by reference herein. Furthermore, the suture may include portions which are monofilament and portions which are multifilament.

Once the suture is constructed, it can be sterilized by any means within the purview of those skilled in the art.

Sutures in accordance with the present disclosure may be coated or impregnated with one or more medico-surgically useful substances, e.g., bioactive agents which accelerate or beneficially modify the healing process when the suture is applied to a wound or surgical site. Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial to the animal and tend to promote the healing process. For example, a suture can be provided with a bioactive agent that may be deposited at the sutured site. The bioactive agent can be chosen for its antimicrobial properties, capability for promoting wound repair and/or tissue growth, or for specific indications such as thrombosis. In embodiments, combinations of such agents may be applied to a suture of the present disclosure.

The term "antimicrobial agent" as used herein includes an agent, which by itself or through assisting the immune system, helps the body destroy or resist microorganisms which may be pathogenic. An antimicrobial agent includes antibiotics, antiseptics, quorum sensing blockers, antifungals, antivirals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following anti-microbial agents may be used alone or in combination with other bioactive agents described herein: an anthracycline, doxorubicin, mitoxantrone, a fluoropyrimidine, 5-fluorouracil (5-FU), a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Syneroid, clarithromycin, and kanamycin sulfate), tetracyclines like minocycline, fusidic acid, trimethoprim, metronidazole, a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Examples of antiseptics and disinfectants which may be utilized as the antimicrobial agent include hexachlorophene; cationic biguanides like chlorhexidine and cyclohexidine; iodine and iodophores like povidone-iodine; ionic silver, ionic silver glasses, halo-substituted phenolic compounds like PCMX (i.e., p-chloro-m-xylenol) and triclosan (i.e., 2,4, 4'-trichloro-2' hydroxy-diphenylether); furan medical preparations like nitrofurantoin and nitrofurazone; methenamine; aldehydes like glutaraldehyde and formaldehyde; and alcohols. In some useful embodiments, at least one of the antimicrobial agents may be an antiseptic such as triclosan.

To promote wound repair and/or tissue growth, one or more bioactive agents known to achieve either or both of these objectives can also be applied to the suture as wound repair agents or tissue growth agents. Such clotting or "fibrosis-inducing agents" are utilized for the promotion of aneurysm or embolism when it is desired for treatment of particular vascular insults or diseases, or for example, blocking a tumor from its primary blood supply. In embodiments, the barbed suture having a clotting agent deposited within the barb angles in accordance with the present disclosure may contribute to platelet and blood component capture.

Examples of chemotherapeutics which may be utilized include one or more of the following: doxorubicin (Dox), paclitaxel (PTX), or camptothecin (CPT), polyglutamate-PTX (CT-2103 or Xyotax), N-(2-hydroxypropyl)methacrylamide (HPMA) copolymer, anthracycline, mitoxantrone, letrozole, anastrozole, epidermal growth factor receptor inhibitors, tyrosine kinase inhibitors, modulators of apoptosis, anthracycline antibiotics such as daunorubicin and doxorubicin, alkylating agents such as cyclophosphamide and melphalan, antimetabolites such as methotrexate and 5-fluorouracil, poly(ethylene glycol) (PEG), poly(glutamic acid) (PGA), polysaccharides, monoclonal antibody and polymer-drug conjugates thereof, copolymers thereof and combinations thereof.

The clotting agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly(ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs (L-azetidine-2-carboxylic acid (LACA), cishydroxyproline, d,L-3,4-dehydroproline, Thiaproline, α,α-dipyridyl, β-aminopropionitrile fumarate); MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin Gold Sodium Thiomalate ("GST"); D-Penicillamine ("CDPT"); β-1-anticollagenase-serum; α2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Sutures in accordance with this disclosure can also include, for example, biologically acceptable plasticizers, antioxidants and colorants, which can be impregnated into the filament(s) utilized to form a suture of the present disclosure or included in a coating thereon.

As noted above, bioactive agents may be impregnated into the materials utilized to form sutures of the present disclosure or deposited on the surface thereof. Bioactive agents may be applied onto a barbed suture of the present disclosure utilizing any method within the purview of one skilled in the art including, for example, dipping, spraying, vapor deposition, brushing, compounding and the like.

In embodiments the bioactive agent, such as an antimicrobial agent, may be applied to a barbed suture of the present disclosure as part of a bioactive agent solution. The bioactive agent solution can include any solvent or combination of solvents suitable for the chosen bioactive agent. To be suitable, the solvent should (1) be miscible with the bioactive agent, and (2) not appreciably affect the integrity of any material used to form a medical device, such as the barbed suture. In some useful embodiments, the solvent utilized is a polar solvent. Some examples of suitable solvents include methylene chloride, chloroform, ethyl acetate, methyl acetate, N-methyl 2-pyrrolidone, 2-pyrrolidone, propylene glycol, tetrahydrofuran (THF), acetone, oleic acid, methyl ethyl ketone, water, and mixtures thereof. In one embodiment, methylene chloride may be used as a solvent.

The method of preparing the bioactive agent solution can be a relatively simple procedure including mixing, blending, and the like. Any known technique may be employed for applying the bioactive agent solution to the medical device. Suitable techniques include dipping, spraying, wiping, brushing, and the like.

The bioactive agent solution generally contains from about 0.1% to about 20% of the bioactive agent by weight, in embodiments from about 0.5% to about 5% of the bioactive agent by weight. The exact amount of the bioactive agent will depend on a number of factors, such as the particular agent used, the medical device being contacted and the choice of solvent employed. In one embodiment, where the bioactive agent is an antimicrobial agent, the antimicrobial solution may contain from about 0.1% to about 10% of the chosen antimicrobial agent, in embodiments from about 1% to about 5% of the antimicrobial agent.

The amount of the bioactive agent solution applied should be an effective amount to provide the desired bioactive properties to the suture. The exact amount will depend upon the configuration of the suture and the formulation of the solution. Since the bioactive agent solution contains a solvent, a curing step may be employed in useful embodiments to remove the solvent, leaving the bioactive agent on the suture. Suitable curing steps for removal of the solvent include, but are not limited to, evaporation and/or lyophilization. Upon removal of the solvent, the bioactive agent remains bound to the suture in the angle formed between the barb and suture body.

Regardless of the method of application, the amount of the bioactive agent on the suture can be from about 0.01% by weight of the suture to about 2% by weight of the suture, in embodiments from about 0.02% by weight of the suture to about 1% by weight of the suture, typically from about 0.05% by weight of the suture to about 0.5% by weight of the suture.

Once applied, the bioactive agent will not be lost due to evaporation, sublimation, volatilization, etc. during the subsequent handling, processing and storage of the barbed suture. However, upon application of the barbed suture in vivo, that is, after use in suturing a wound, the attachment of the barbs to the tissue will release the bioactive agent into the tissue.

In other embodiments, the bioactive agent may be included in a coating applied to the suture. Suitable coatings which may be utilized are within the purview of one skilled in the art and include, for example, biodegradable coatings such as those disclosed in U.S. Patent Publication No. 20040153125, the entire disclosure of which is incorporated by reference herein. Suitable coatings may include trimethylene carbonate, tetramethylene carbonate, caprolactone, valerolactone, dioxanone, glycolic acid, lactic acid, glycolides, polyanhydrides, polyesters, polyacrylates, polymethylmethacrylates, polyurethanes, polyorthoester, polyhydroxy alkanoates, polytribolate, polyhydroxy butyrate, lactides, polymer drugs, homopolymers thereof, copolymers thereof, and combinations thereof. Biodegradable polymers may be suitable as they will release the bioactive agent in vivo as the biodegradable polymer is resorbed by the body.

In embodiments, mixtures useful in forming the aforementioned coatings include a bioactive agent such as an antimicrobial agent as a predominant component in an effective antimicrobial amount. A "predominant amount" refers to one or more components which are present in an amount greater than about 50 weight percent. A "minor amount" refers to one or more components which are present in an amount up to about 50 weight percent. The minor component may include copolymers containing biodegradable monomers such as caprolactone.

An "effective antimicrobial amount" of a given component is an amount at which the component hinders the growth of bacteria to diminish or avoid contamination of the wound site.

In embodiments, the antimicrobial degradable coating composition for biocompatible surgical implantable devices is inexpensive, biocompatible, and not subject to excessive diffusion. "Biocompatible" means that no serious systemic toxicity is caused by the presence of an object in a living system. It is contemplated that biocompatible objects may cause some clinically acceptable amounts of toxicity including irritation and/or other adverse reactions in certain individuals.

Any biodegradable polymer within the purview of those skilled in the art can be employed in the present coatings. In embodiments, the biodegradable polymer may contain epsilon-caprolactone as a component thereof. Suitable caprolactone containing copolymers include copolymers which may be synthesized by well known conventional polymerization techniques. In some embodiments, suitable caprolactone containing copolymers are "star" copolymers obtained by polymerizing a predominant amount of epsilon-caprolactone and a minor amount of another biodegradable monomer polymerizable therewith in the presence of a polyhydric alcohol initiator.

In embodiments, the caprolactone containing copolymer may be obtained by polymerizing a predominant amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

In certain embodiments, the copolymer herein can contain from about 70 to about 98, and preferably from about 80 to about 95, weight percent epsilon-caprolactone derived units, the balance of the copolymer being derived from the other copolymerizable monomer(s).

Suitable monomers which can be copolymerized with epsilon-caprolactone include alkylene carbonates such as trimethylene carbonate, tetramethylene carbonate, dimethyl trimethylene carbonate; dioxanones; dioxepanones; degradable cyclic amides; alkylene oxides such as polyethylene oxide (PEO) and polypropylene oxide (PPO), degradable cyclic ether-esters derived from crown ethers; hydroxyacids capable of esterification, including both alpha hydroxyacids (such as glycolic acid and lactic acid) and beta hydroxyacids (such as beta hydroxybutyric acid and gamma hydroxyvaleric acid); polyalkyl ethers (such as polyethylene glycol (PEG) and polypropylene glycol (PPG) and combinations thereof); polyvinyl pyrrolidone, hydroxyethylmethacrylate; phosphorylcholine; acrylic acid; methacrylic acid; vinyl monomers; vinyl alcohols; vinyl acetate; and combinations thereof. In embodiments, a suitable monomer for use with the present disclosure is glycolide.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis(2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like; with mannitol being preferred.

The polyhydric alcohol initiator is generally employed in relatively small amounts, e.g., from about 0.01 to about 5, and preferably from about 0.1 to about 3, weight percent of the total monomer mixture.

The coating composition can contain from about 0.3 to about 10, and preferably from about 0.5 to about 5, weight percent of the copolymer. Such a coating provides sutures with the combined desirable properties of improved handling characteristics and antimicrobial activity.

In addition to the antimicrobial agents described above, in some embodiments the coating may include one or more fatty acid components such as fatty acids, fatty acid salts and salts of fatty acid esters which may impart antimicrobial characteristics to the suture.

Where the coating includes a fatty acid metal salt, the fatty acid metal salt used as the antimicrobial agent may include metal stearates. In one embodiment, the fatty acid salt used as the antimicrobial agent is silver stearate. In another embodiment, the fatty acid salt(s) used as the antimicrobial agent may be combined with fatty acid esters such as stearoyl lactylates, particularly calcium stearoyl lactylate.

Suitable fatty acids which can be used in the present coatings include the biocompatible monovalent and polyvalent metal salts of fatty acids having 6 or more carbon atoms. Examples of fatty acids useful for forming a metal salt of a fatty acid useful herein includes butyric, caproic, caprylic, capric, lauric, myristic, palmitic, palmitoleic, stearic, oleic, linoleic, linolenic, etc. Examples of monovalent metals useful for forming a metal salt of a fatty acid useful in the various embodiments described herein include lithium, rubidium, cesium, francium, copper, silver and gold. Examples of polyvalent metals useful for forming a metal salt of a fatty acid useful in the various embodiments described herein include aluminum, tin, lead, bismuth and the polyvalent transition metals. Therefore, suitable metal salts of fatty acids useful herein include fatty acid salts of lithium, rubidium, cesium, francium, copper, silver, gold, beryllium, magnesium, strontium, barium, radium, aluminum, tin, lead, bismuth, zinc, cadmium, mercury, etc.

The metal salt of a fatty acid is present in the coating composition in an effective antimicrobial amount as defined above. The metal salt of a fatty acid can consist of a single chemical compound. However, the metal salt of a fatty acid can also be a mixture of several metal salts of fatty acids. The metal salt of a fatty acid may be present in an amount from about 30 percent to about 70 percent by weight of the coating composition, in embodiments from about 45 percent to about 55 percent by weight of the coating composition.

The metal salt of a fatty acid may be relatively insoluble in cold water. When desirable, a solvent may be used to improve the working properties, e.g., viscosity, miscibility, etc., of the metal salt of a fatty acid. Suitable solvents include, for example, alcohols, e.g., methanol, ethanol, propanol, chlorinated hydrocarbons (such as methylene chloride, chloroform, 1,2-dichloro-ethane), and aliphatic hydrocarbons (such as hexane, heptene, ethyl acetate). When desirable, heat may be applied to the solvent mixture of metal salts of fatty acids to improve their solubility. For example, temperatures ranging from about 30° C. to about 60° C. are appropriate.

In certain embodiments, fatty acid esters may be combined with the metal salt of a fatty acid in the coating composition. Such esters include, for example, calcium stearate, stearoyl lactylate esters, palmityl lactylate esters, oleyl lactylate esters such as calcium, magnesium, aluminum, barium, or zinc stearoyl lactylate; calcium, magnesium, aluminum, barium, or zinc palmityl lactylate; calcium, magnesium, aluminum, barium, or zinc oleyl lactylate; with calcium stearate and calcium stearoyl-2-lactylate (such as the calcium stearoyl-2-lactylate commercially available under the tradename VERV from American Ingredients Co., Kansas City, Mo.) being preferred. When desirable, the fatty acid ester may be combined with a solvent. Suitable solvents include those listed above.

Where the bioactive agent is included as part of a coating, the bioactive agent and coating components may be added to separate solvents, and the resulting solvent mixtures may then be combined to form a coating solution. In other embodiments, the bioactive agent and coating components may be combined together and then mixed with solvent to form a coating solution or any combination. The order of addition is not critical and therefore may be determined through routine experimentation depending upon the desired use.

The coating can be applied to a suture by any suitable process, e.g., passing the suture through a solution of the coating mixture, past a brush or other coating solution applicator, or past one or more spray nozzles dispensing the suture coating solution. The coating solution can contain from about 30 to about 70, in embodiments from about 45 to about 55, weight percent solvent. In embodiments, a mixture of methylene chloride, hexane and ethanol may be used as a solvent. The suture wetted with the coating solution may be optionally passed through or held in a drying oven for a time and at a temperature sufficient to vaporize and drive off the solvent. If desired, the suture coating composition can optionally contain additional bioactive agents or components described above, e.g., dyes, antibiotics, antiseptics, growth factors, anti-inflammatory agents, etc.

Barbs may be formed on the surface of the body of a suture utilizing any method within the purview of one skilled in the art. Such methods include, but are not limited to, cutting, molding, and the like. In some embodiments, barbs may be formed by making acute angular cuts directly into the suture body, with cut portions pushed outwardly and separated from the body of the suture. The depth of the barbs thus formed in the suture body may depend on the diameter of the suture material and the depth of the cut. In some embodiments, a suitable device for cutting a plurality of axially spaced barbs on the exterior of a suture filament may include a cutting bed, a cutting bed vise, a cutting template, and a blade assembly to perform the cutting. In operation, the cutting device has the ability to produce a plurality of axially spaced barbs in the same or random configuration and at different angles in relation to each other. Other suitable methods of cutting the barbs include the use of a laser or manual methods. The suture could also be formed by injection molding, extrusion, stamping and the like. The suture can be packaged in any number of desired pre-cut lengths and in pre-shaped curves.

In embodiments, all of the barbs may be aligned to allow the suture to move through tissue in one direction and resist moving through tissue in the opposite direction. For example, referring to FIG. 1, the barbs 12 on a suture 10 may be formed into a single directional suture. In embodiments suture 10 may be attached to needle 16. The barbs 12 are yieldable toward the body 14 of suture 10. The barbs 12 permit movement of suture 10 through tissue in the direction of movement of a needle end 16 but are generally rigid in an opposite direction and prevent movement of suture 10 in a direction opposite the direction of movement of a needle end 16.

Suture 10 may include a bioactive agent (not shown) disposed within the angle between the barb 12 and suture body 14.

Alternatively, a multifilament suture (not shown) may be utilized which may include filaments fabricated from biocompatible degradable polymers, biocompatible non-degradable polymers, or combinations thereof. In embodiments, a multifilament suture may be provided which includes a biocompatible degradable polymer which includes a bioactive agent disposed within the angle between the barb and suture body. In another embodiment, a multifilament suture may include individual filaments fabricated from a combination of biocompatible degradable polymer or biocompatible non-degradable polymer which includes a bioactive agent disposed within the angle between the barb and suture body.

Figure 2:
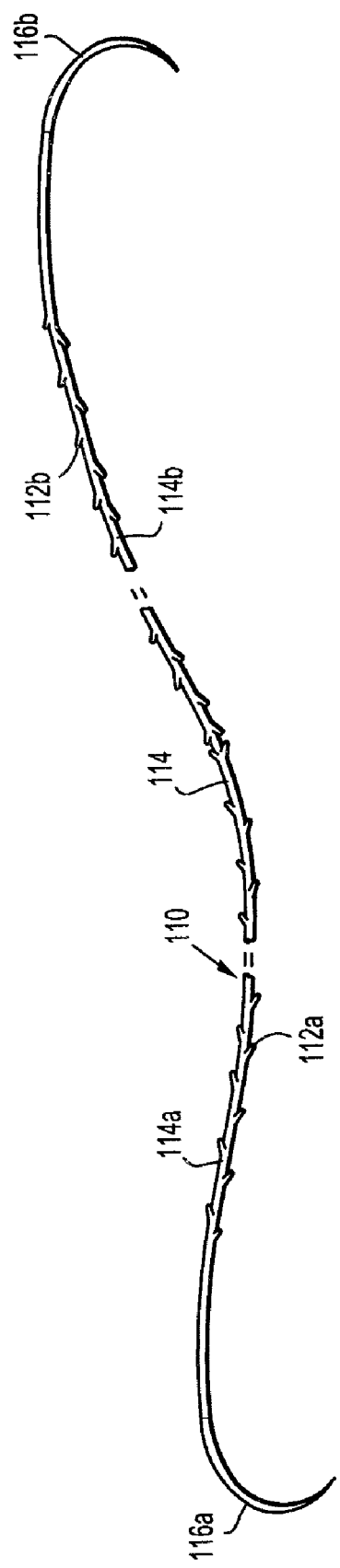
FIG. 2 is a perspective view of a bi-directional barbed suture attached to a needle on each end.

In other embodiments, the barbs may be aligned on a first portion of a length of a suture to allow movement of a first end of the suture through tissue in one direction, while barbs on a second portion of the length of the suture may be aligned to allow movement of the second end of the suture in an opposite direction. For example, as depicted in FIG. 2, a suture 110 may be bi-directional. Barbed suture 110 includes an elongated body 114 having two areas, body portion 114*a* and body portion 114*b*, distal first and second needle ends 116*a* and 116*b* for penetrating tissue, and a plurality of barbs 112*a* and 112b extending from the periphery of the body 114. An antimicrobial agent may be disposed within the angle formed between the barbs 112a and 112b and suture body 114. Barbs 112a on a first portion of the body 114a between the first end of suture 110 and a first axial location on the suture body permit movement of suture 110 through the tissue in a direction of movement of first needle end 116a and prevent movement of suture 110 relative to the tissue in a direction opposite the direction of movement of the first needle end 116a. Barbs 112b on second portion of body 114b between a second needle end 116b of a suture 114 and a second axial location on the body which is less than the distance from the second needle end 116b to the first axial location permit movement of a suture 114 through the tissue in a direction of movement of a second needle end 116b and prevent movement of a suture 114 relative to the tissue in a direction opposite the direction of movement of the second needle end 116b.

The barbs can be arranged in any suitable pattern, for example, in a helical pattern. The number, configuration, spacing and surface area of the barbs can vary depending upon the tissue in which the suture is used, as well as the composition and geometry of the material utilized to form the suture. Additionally, the proportions of the barbs may remain relatively constant while the overall length of the barbs and the spacing of the barbs may be determined by the tissue being connected. For example, if the suture is to be used to connect the edges of a wound in skin or tendon, the barbs may be made relatively short and more rigid to facilitate entry into this rather firm tissue. Alternatively, if the suture is intended for use in fatty tissue, which is relatively soft, the barbs may be made longer and spaced further apart to increase the ability of the suture to grip the soft tissue.

The surface area of the barbs can also vary. For example, fuller-tipped barbs can be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum anchoring properties. In embodiments a single directional suture as depicted in FIG. 1 may have both large and small barbs; in other embodiments a bi-directional suture as depicted in FIG. 2 may have both large and small barbs.

In embodiments, sutures of the present disclosure may be dyed in order to increase the visibility of the suture in the surgical field. Any dye suitable for incorporation in sutures can be used. Such dyes include, but are not limited to, carbon black, bone black, D&C Green No. 6, and D&C Violet No. 2. In embodiments, sutures in accordance with the present disclosure may be dyed by adding dye in an amount up to about a few percent, in other embodiments by adding dye in an amount of about 0.2%, in still further embodiments in an amount from about 0.06% to about 0.08%.

In order to facilitate needle attachment to a suture of the present disclosure, conventional tipping agents can be applied to the braid. Two tipped ends of the suture may be desirable for attaching a needle to each end of the suture to provide a so-called double armed suture. The needle attachment can be made by any conventional method such as crimping, swaging, etc, as is known within the purview of those skilled in the art. Wounds may be sutured by passing the needled suture through tissue to create wound closure. The coating, in addition to enhancing the suture's handling characteristics, advantageously possesses antimicrobial properties to promote healing and prevent infection.

In some embodiments, the barb contribution to the architecture of the suture or a wound closure device may contribute to platelet and blood component capture. Referring to FIGS. 3A, 3B, 3C, a tubular insertion device 22 may be utilized to introduce a barbed suture 10 in accordance with the present disclosure into a blood vessel 20. Such a tubular insertion device 22 may have a tubular body in which the barbed suture 10 is disposed, as well as a distal end 24 and a proximal end 26. In use, the pointed end of a barbed suture 10 of the present disclosure may be pushed with the distal end 24 of the tubular insertion device through skin, tissue, vessels, and the like at an insertion point. The pointed end of barbed suture 10 and the distal end 24 of the tubular insertion device are pushed through the tissue until reaching an endpoint. The proximal end 26 of the tubular insertion device 22 is then gripped and pulled to remove the insertion device 22, leaving the barbed suture 10 in place.

For ease of movement of the tubular insertion device, the tubular insertion device 22 may include a string, wire, or the like to pull and remove the insertion device 22 from the barbed suture as illustrated in FIG. 3B. In exemplary embodiments, the tubular insertion device 22 is deployed from barbed suture 10, which allows for barbed suture 10 to expand to full vessel thickness and anchor itself to the vessel 20. As illustrated in FIG. 3C, the deployment of tubular insertion device 22 and expansion of the barbed suture 10 allows for the capture of circulating platelets and blood components to instigate vascular blockage and/or clotting of vessel 20.

The barbed suture in FIGS. 3A-3C illustrates a flexible and bent configuration. However, it is envisioned that a variety of suture or fiber configurations may be employed. In other embodiments, fiber configurations may include twisting the barbed device within the sheath (not shown).

In an exemplary embodiment, where present, a tubular insertion device surrounding a barbed suture of the present disclosure protects the bioactive agent which is disposed within the barb angle formed by the barb and the suture body. Thus, the tubular insertion device may aid in keeping the barbed suture intact and the bioactive agent attached to the body of the suture during insertion, as well as during handling, and storage of the suture. This minimizes the loss of bioactive agent to the packaging of the medical device, the environment, etc. However, upon engaging the barbed suture and tubular insertion device in vivo, moving the sheath relative to the suture to extract the sheath from the tissue exposes the bioactive agent to tissue and assists in the release of bioactive agent from the interface of the barb and the suture body into the wound closure. The barbed suture expands to full vessel thickness and acts as an anchor to patient tissue.

Figure 5A:
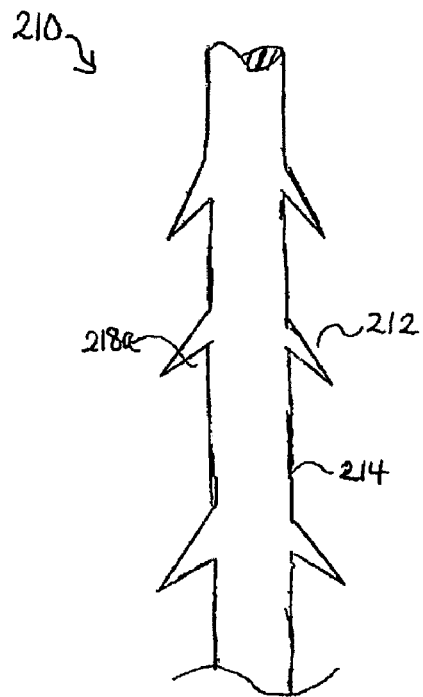
FIGS. 5A-5B are plan views of a portion of a barbed suture having shape memory polymer barbs in permanent and temporary configurations, respectively, in accordance with an embodiment of the present disclosure.
Figure 5B:
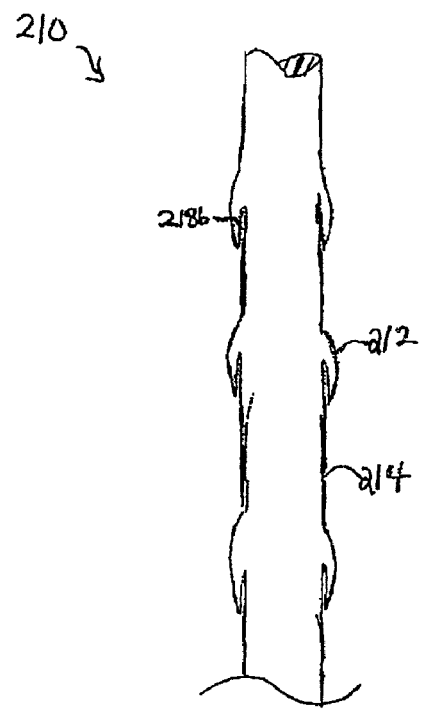

In another exemplary embodiment, the bioactive agent may be protected and/or the release of the bioactive agent may be controlled by the use of shape memory polymers in the suture body and/or barbs as described above. For example, a suture may include a bioactive agent disposed within the barb angle formed by the barb and the suture body when the suture is in its permanent shape. As illustrated in FIG. 5A, barb 212 extends outwardly and away from body 214 of suture 210 thereby forming barb angle 218a between barb 212 and body 214 of suture 210. The suture may then be deformed into a temporary shape, as illustrated in FIG. 5B, in which the barbs 212 are pressed against the suture body 214 and the barb angles 218b are smaller than the barb angles 218a of the permanent shape, e.g., closed, thereby minimizing the exposure and/or loss of the bioactive agent from the suture 210. As illustrated in FIG. 5B, in the temporary shape, barbs 212 are substantially parallel to the longitudinal axis of body 214 of suture 210 to form barb angle 218b. Upon placement within tissue, the barbs may extend away from the suture body back to their permanent shape, thereby exposing and/or releasing the bioactive agent to tissue. In embodiments, the bioactive agent is released from the barb angles as the barbs transition from the temporary shape as depicted in FIG. 5B to its permanent shape as depicted in FIG. 5A.

In some embodiments, the suture may include multiple barbs having different shape recovery temperatures, thereby providing controlled and sustained release of the bioactive agent, or multiple bioactive agents, into the tissue. In embodiments, a portion of the barbs may recover their permanent shape upon exposure to body temperature and another portion of barbs may recover their permanent shape upon exposure to heat or electric stimuli. In other embodiments, a portion of the barbs may recover their permanent shape upon exposure to a temperature greater than room temperature, but lower than body temperature, with other barbs recovering their permanent shape upon exposure to body temperature. Such a suture may thus possess barbs that recover their permanent shape upon implantation or shortly thereafter, in embodiments from about 1 to about 5 seconds after implantation, with the remaining barbs adopting their permanent shape after reaching body temperature, in embodiments more than 5 seconds after implantation.

In embodiments where a clotting agent is employed, the barbed suture also captures circulating platelets and blood components and instigates vascular blockage or clotting. If mechanical property requirements are not too restrictive, a hydrogel or super-absorbent material may be used to further concentrate blood components, or the barbed device may also drive and place the hydrogel-like material to final placement.

Referring to FIGS. 4A-4B, a sheath 23 may be utilized to introduce barbed suture 10 in accordance with the present disclosure into blood vessel 20. Such a sheath 23 may have a tubular body in which the barbed suture 10 is disposed. In one embodiment, sheath 23 may be disposed at one end of barbed suture 10 and in other embodiments, sheath 23 may be disposed on both ends of barbed suture 10 (not shown). In embodiments, sheath 23 may be formed of materials such as, but are not limited to, filament fibers, nylon fibers, polyester (PET), copolymer polyester (co-PET), polypropylene (PP), and polyethylene (PE) which are designed to swell in order to block vessel 20 and induce clotting as the barbs on the suture, fully engaged and expanded within vessel 20, captures blood components and platelets to assist in the clotting. The barbed suture 10 may also include a bioactive agent within the included angle of the barb and the elongated body of the suture to enhance clotting of vessel 20.

Methods for repairing tissue with the sutures of the present disclosure are also provided. The sutures of the present disclosure may be utilized in any cosmetic endoscopic or laparoscopic methods. In addition, sutures of the present disclosure may be utilized to attach one tissue to another including, but not limited to, attaching tissue to a ligament.

In embodiments, sutures of the present disclosure may be held in place without the need for knots. In such cases, tissue located over a suture of the present disclosure placed in vivo may be physically manipulated or massaged into a desired position to enhance the holding of tissue in the desired position. In embodiments, the physical manipulation of tissue located over a suture of the present disclosure may enhance the release of any medicinal agent located on the suture, including any medicinal agent found in the angle between a barb and the body of a suture of the present disclosure.

For example, sutures of the present disclosure may be utilized to provide lift to tissue, which may be desirable in certain cosmetic applications. In embodiments, a procedure for closing tissue utilizing sutures includes inserting a first end of a suture, optionally attached to a needle, at an insertion point on the surface of a person's body. The first end of the suture may be pushed through soft tissue until the first end extends out of the soft tissue at an exit point. The first end of the suture may then be gripped and pulled to draw the first portion of the suture through the soft tissue so that a length of the first portion of the suture remains in the soft tissue between the point of insertion and exit point of the first end. The soft tissue may then be manually grouped and advanced along at least one portion of the suture to provide the desired amount of lift.

Specific applications of cosmetic surgeries which may utilized this physical manipulation of a suture as described above include, for example, facelifts, browlifts, thigh lifts, and breast lifts.

While the above description contains many specifics, these specifics should not be construed as limitations on the scope of the disclosure, but merely as exemplifications of embodiments thereof. Those skilled in the art will envision many other possibilities, including the use of other wound closure devices, within the scope and spirit of the disclosure as defined by the claims appended hereto.

What is claimed is:

1. A method of releasing a bioactive agent from a suture comprising:
    providing a suture in a temporary shape, the suture comprising:
        an elongated body;
        a plurality of barbs extending from the elongated body and forming a barb angle between an inner surface of the barbs and an outer surface of the elongated body, at least a portion of the plurality of barbs being made from a shape memory polymer having a temporary shape in which the barbs are compressed against the elongated body; and
        an effective amount of a bioactive agent disposed within the barb angles formed between the inner surface of the barbs and the outer surface of the elongated body; and
    placing the suture into tissue such that the barbs recover from the temporary shape into a permanent shape in which the barbs extend outwardly and away from the elongated body, thereby releasing the bioactive agent from the barb angles and into the tissue.

2. The method of claim 1, wherein providing the suture includes providing the suture in a temporary shape such that the plurality of barbs extend substantially parallel with a longitudinal axis of the suture.

3. The method of claim 1, wherein releasing the bioactive agent into the tissue includes releasing the bioactive agent from the barb angles upon transitioning of the plurality of barbs from the temporary shape to the permanent shape.

4. The method of claim 1, wherein providing the suture includes providing a first portion of the plurality of barbs with first recovery temperature and a second portion of the plurality of barbs with a second recovery temperature, thereby providing controlled and sustained release of the bioactive agent upon placement into tissue.

5. The method of claim 4, wherein placing the suture into tissue further comprises recovering the permanent shape of the first portion of the plurality of barbs upon exposure to body temperature.

6. The method of claim 5, further comprising applying an electric stimuli to recover the permanent shape of the second portion of the plurality of barbs.

* * * * *